US006153585A

United States Patent [19]
Rubenstein et al.

[11] Patent Number: 6,153,585
[45] Date of Patent: Nov. 28, 2000

[54] ARYLSULFONANILIDE DERIVATIVES

[75] Inventors: Steven M. Rubenstein, Pacifica; Juan C. Jaen, Burlingame, both of Calif.

[73] Assignee: Tularik Inc., So. San Francisco, Calif.

[21] Appl. No.: 09/353,976

[22] Filed: Jul. 15, 1999

Related U.S. Application Data

[60] Provisional application No. 60/093,570, Jul. 20, 1998.

[51] Int. Cl.⁷ .................................................. A61K 38/00
[52] U.S. Cl. .................................. 514/14; 514/2; 514/15; 514/16; 514/17; 514/18; 514/19; 514/9; 514/11; 514/464; 514/238.8; 514/518; 514/602; 514/604; 549/434; 558/56; 558/61; 564/90
[58] Field of Search ..................................... 530/300, 317, 530/328–330; 514/2, 14–19, 9, 11, 464, 238.8, 518, 602, 604; 549/434; 558/56, 61; 564/90

[56] References Cited

U.S. PATENT DOCUMENTS

| | | | |
|---|---|---|---|
| 1,955,207 | 4/1934 | Stotter et al. | 167/37 |
| 2,358,365 | 9/1944 | Tullar | 260/397.6 |
| 2,402,623 | 6/1946 | Hester et al. | 268/546 |
| 3,034,955 | 5/1962 | Frick et al. | 167/37 |
| 4,881,969 | 11/1989 | Saupe et al. | 71/94 |
| 4,883,914 | 11/1989 | Alvarado et al. | 564/91 |
| 4,900,867 | 2/1990 | Wilkes et al. | 564/91 |
| 5,143,937 | 9/1992 | Lang et al. | 514/603 |

(List continued on next page.)

FOREIGN PATENT DOCUMENTS

| | | |
|---|---|---|
| 0 391 799 | 10/1990 | European Pat. Off. . |
| 0 469 901 | 2/1992 | European Pat. Off. . |
| 0 472 449 | 2/1992 | European Pat. Off. . |
| 622 494 | 11/1935 | Germany . |
| 36 23 184 | 1/1988 | Germany . |
| 859 345 | 1/1961 | United Kingdom . |
| 938 890 | 10/1963 | United Kingdom . |
| 1 189 720 | 4/1970 | United Kingdom . |
| 1 242 057 | 8/1971 | United Kingdom . |
| 1 306 564 | 2/1973 | United Kingdom . |
| WO 97/30677 A2 | 8/1997 | WIPO . |
| WO 98/05315 | 2/1998 | WIPO . |

OTHER PUBLICATIONS

Fielding et al, "Synthesis and Reactions of 4–sulpho–2,3,5, 6–Tetrafluorobenzoic Acid"; *Journal of Fluorine Chemistry*, vol. 59, No. 1, pp. 15–31 (1992).

Raibekas et al. "Affinity Probing of Flavin Binding Sites. 2. Identification of Reactive cysteine in the Flavin Domain of *Escherichia coli* DNA Photolyase"; *Biochemistry*, vol. 33, No. 42, pp. 12656–12664 (1994).

Shealy et al. "2–Haloethylating Agents for Cancer Chemotherapy. 2–Haloethyl Sulfonates"; *Journal of Medicinal Chemistry*, vol. 26, pp. 1168–1173 (Aug. 1983).

Olander et al., "A Study of the binding of two sulfonamides to Carbonic Anhydrase"; *Journal of American Chemical Society*, vol. 95, No. 5, pp. 1616–1621 (Mar. 7, 1973).

Hawkinson, et al; "Studies of the Solvolysis of 2–Adamantyl Pentafluorobenzenesulfonate: A $Y_{PFBS}$ Scale"; *The Journal of Organic Chemistry*, Aug. 1988, vol. 53, No. 16, pp. 3857–3860.

Chemical Abstracts, vol. 50, No. 1, Jan. 10, 1956 Columbus, Ohio, US; abstract No. 217g, V.O. Lukashevich: "Sulphonation of halogen–substituted benzene derivatives. formation of anhydrides of corresponding sulphonic acids" column 217; XP002083056 see abstract & Doklady Akad. Nauk S.S.S.R., vol. 99, 1954, pp. 995–998.

Chemical Abstracts, vol. 74, No. 14, Apr. 5, 1971, Columbus, Ohio, US; abstract No. 65535a, D. Simov, Et al.: "Preparation of azo dyes containing amobile chlorine atom in the benzene ring" p. 81: XP002083055 see abstract & Izv. Otd. Khim. Nauki, Bulg. Akad. Nauk, vol. 3, No. 1, 1970, pp. 69–82.

I.C. Poppoff, et al.: "Antimalarial agents. 8. Ring–substituted bis–(4–aminophenyl) sulphones and their precursors" *Journal of Medicinal Chemistry*, vol. 14, No. 12, Dec. 1971, pp. 1166–1169, XP002083052 Washington, FC, US see compounds V, VIII,X, XI, XIII, XVII, XIX, XXVIII, XXXII, XXXVI–XXXVIII, XLI, XLII<XLIV<XLV.

G.E. Chivers, et al.: "Studies in the chemistry of polyhalogenobenzene compounds. The synthesis and reactivity of 2,3,5,6– and 2,3,4,5,–tetrachlorobenzenesulphonyl chlorides and related compounds"; *Australian Journal of Chemistry*, vol. 29, No. 7, Jul. 1976, pp. 1572–1582, XP002083174, Melbourne, AU.

P.G. DeBenedetti, et al.; "Quantitative structure–activity analysis in dihydropteroate synghase inhibition by sulphones. Comparison with sulphanilamides" *Journal of Medicinal Chemistry*, vol. 30, No. 3, Mar. 1987, pp. 459–464. XP002083053 Washington, DC, US.

V.N. Babushkin, et al.: "Influence of substituents on the frequency of stretching vibrations of sulphur–containing bridging groups in diphenyl systems" *Journal of General Chemistry of the USSR*, vol. 58, No. 7, pt. 2, Jul. 1988., pp. 1457–1460. XP002083054 New York, US.

Yoshimoto and Hansch, "Correlation Analysis of Baker's Studies on Enzyme Inhibition. 2. Chymotrypsin, Thymidine Phosphorylase, Uridine Phosphorylase, Thymidylate Synthetase, Cytosine Nucleoside Deaminase, Dihydrofolate Reductase, malate Dehydrogenase, Glutamate Dehydrogenase, Lactate Dehydrogenase, and Glyceraldehyde–phosphate Dehydrogenase."; *Journal of Medicinal Chemistry* (1976) vol. 19, No. 1 pp. 71–98.

(List continued on next page.)

*Primary Examiner*—Bennett Celsa
*Attorney, Agent, or Firm*—Townsend and Townsend and Crew LLP

[57] ABSTRACT

The invention provides compounds, compositions and methods relating to novel arylsulfonanilide derivatives and their use as pharmacologically active agents. The compositions find particular use as pharmacological agents in the treatment of disease states, particularly cancer, psoriasis, vascular restenosis, infections, atherosclerosis and hypercholesterolemia, or as lead compounds for the development of such agents.

37 Claims, No Drawings

U.S. PATENT DOCUMENTS

| | | | |
|---|---|---|---|
| 5,189,211 | 2/1993 | Sato et al. | 562/430 |
| 5,250,549 | 10/1993 | Yoshino et al. | 514/345 |
| 5,385,931 | 1/1995 | Bigg et al. | 514/443 |
| 5,387,709 | 2/1995 | Lardy et al. | 558/388 |
| 5,880,151 | 3/1999 | Medina et al. | 514/518 |

OTHER PUBLICATIONS

Bai, et al.; "Identification of the cystein Residue of β–Tubulin Alkylated by the Antimitotic Agent 2,4–Dichlorobenzyl Thiocyanate, Facilitated by Separationof the Protein subunits of Tubulin by Hydrophobic column chromatography"; *Biochemistry* 1989, vol. 28, pp. 5606–5612.

ARYLSULFONANILIDE DERIVATIVES

This application claims priority to No. 60/093,570 Jul. 20, 1998.

FIELD OF THE INVENTION

The present invention relates to arylsulfonanilide derivatives and their use as pharmacologically active agents capable of lowering plasma cholesterol levels and inhibiting abnormal cell proliferation.

BACKGROUND

A number of arylsulfonamides have recently been described for the treatment of disorders and conditions arising from abnormal cell proliferation and from elevated plasma cholesterol levels. See, for example, PCT publications WO 97/30677 and WO 98/05315.

Most prevalent among diseases stemming from abnormal cell proliferation is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells, even after prolonged exposure to the drug. Unfortunately, none of the current chemotherapies possess an ideal profile. Most possess very narrow therapeutic indexes and, in practically every instance, cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Accordingly, it is one object of the present invention to provide compounds which directly or indirectly are toxic to actively dividing cells and are useful in the treatment of cancer, viral and bacterial infections, vascular restenosis, inflammatory diseases, autoimmune diseases, and psoriasis.

A further object of the present invention is to provide therapeutic compositions for treating said conditions.

Still further objects are to provide methods for killing actively proliferating cells, such as cancerous, bacterial, or epithelial cells, and treating all types of cancers, infections, inflammatory, and generally proliferative conditions. A further object is to provide methods for treating other medical conditions characterized by the presence of rapidly proliferating cells, such as psoriasis and other skin disorders.

Other objects, features and advantages will become apparent to those skilled in the art from the following description and claims.

SUMMARY OF THE INVENTION

The invention provides novel arylsulfonanilide compounds, as well as methods and compositions relating to novel arylsulfonanilides and their use as pharmacologically active agents. The compounds and compositions find use as pharmacological agents in the treatment of disease states, particularly hypercholesterolemia, atherosclerosis, cancer, bacterial infections, and psoriasis, or as lead compounds for the development of such agents. The compounds of the invention have the formula:

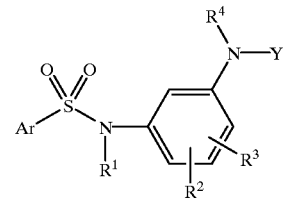

I or a pharmaceutically acceptable salt thereof.

In one group of embodiments the letter Y in the above formula represents a linear or cyclic peptide having from four to fourteen amino acid residues or a radical of formula —Aa—Z, wherein Aa is an amino acid or dipeptide residue and Z is selected from hydrogen, —CHO,

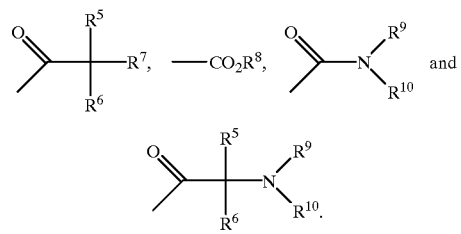

For the radicals above, the symbols $R^5$, $R^6$ and $R^7$ are each independently hydrogen, $(C_1-C_8)$alkyl, $(C_1-C_8)$heteroalkyl, aryl, heteroaryl, aryl$(C_1-C_4)$alkyl, aryl$(C_1-C_4)$heteroalkyl, heteroaryl$(C_1-C_4)$alkyl and heteroaryl$(C_1-C_4)$heteroalkyl.

Optionally, $R^5$ and $R^6$ are linked together to form a 5- or 6-membered ring. The symbol $R^8$ represents $(C_1-C_8)$alkyl, $(C_1-C_8)$heteroalkyl, aryl$(C_1-C_4)$alkyl or aryl$(C_1-C_4)$ heteroalkyl. The symbols $R^9$ and $R^{10}$ are independently hydrogen, $(C_1-C_8)$alkyl, $(C_1-C_8)$heteroalkyl, aryl$(C_1-C_4)$ alkyl and aryl$(C_1-C_4)$heteroalkyl, and are optionally linked together to form a 5- or 6-membered ring.

Returning to the general formula above, the symbols $R^1$ and $R^4$ are each independently hydrogen, $(C_1-C_6)$alkyl or $(C_1-C_6)$heteroalkyl. The symbols $R^2$ and $R^3$ are each independently hydrogen, halogen, $(C_1-C_8)$alkyl, $(C_1-C_8)$ heteroalkyl, $-OR^{11}$, $-SR^{11}$ and $-NR^{11}R^{12}$, wherein $R^{11}$ and $R^{12}$ are each independently hydrogen, $(C_1-C_8)$alkyl and $(C_1-C_8)$heteroalkyl. When $R^2$ and $R^3$ are attached to adjacent carbon atoms, they are optionally linked together to form a fused 5-, 6- or 7-membered ring.

The symbol Ar represents a substituted aryl group selected from

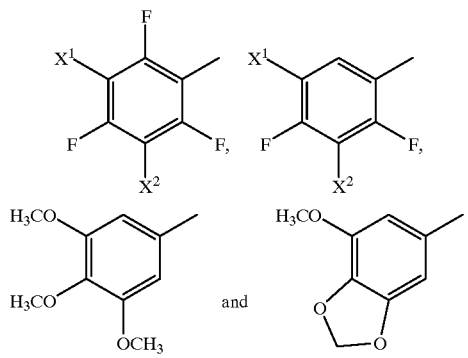

in which $X^1$ and $X^2$ are each independently F, Cl or Br.

The methods of the present invention use pharmaceutical compositions containing compounds of the foregoing description of the general Formula I for the treatment of pathology such as cancer, bacterial infections, psoriasis, hypercholesterolemia, atherosclerosis, pancreatitis, and hyperlipoproteinemia. Briefly, the inventions involve administering to a patient an effective formulation of one or more of the subject compositions.

DETAILED DESCRIPTION OF THE INVENTION

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (ie. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by $-CH_2CH_2CH_2CH_2-$. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "thioalkoxy," employed alone or in combination with other terms means, unless otherwise stated, an alkyl group, as defined above, connected to the remainder of the molecule via a sulfur atom, such as, for example, thiomethoxy (methylthio), thioethoxy (ethylthio), 1-thiopropoxy, 2-thiopropoxy and the higher homologs and isomers.

The term "heteroalkyl," by itself or in combination with another term, means, unless otherwise stated, a stable straight or branched chain, or cyclic hydrocarbon radical, or combinations thereof, which may be fully saturated, mono- or polyunsaturated and can include di- and multi-radicals, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3-CH=CH-O-CH_3$, $-Si(CH_3)_3$, $-CH_2-CH=N-OCH_3$, and $-CH=CH-N(CH_3)-CH_3$. Up to two heteroatoms may be consecutive, such as, for example, $-CH_2-NH-OCH_3$ and $-CH_2-O-Si(CH_3)_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by $-CH_2-CH_2-S-CH_2CH_2-$ and $-CH_2-S-CH_2-CH_2-NH-CH_2-$. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', —halogen, —SiR'R"R'", —OC(O)R', —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted(C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R' and R" are independently selected from hydrogen, (C$_1$–C$_8$)alkyl and heteroalkyl, unsubstituted aryl, (unsubstituted aryl)-(C$_1$–C$_4$)alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

For the compounds of the invention which contain amino acid or peptide fragments, the amino acid residues are denoted by three letter designations following conventional practices. The designations for gene-encoded amino acids are as follows: alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Commonly encountered amino acids which are not gene-encoded may also be used in the present invention. These amino acids include ornithine (Orn), t-butylglycine (t-BuG), phenylglycine (PhG), cyclohexylalanine (Cha), norleucine (Nle), N-methylisoleucine (N-MeIle), homoarginine (Har), sarcosine (Sar), and β-alanine (β-Ala). All of the amino acids used in the present invention may be either the D- or L-isomer. The term "amino acid residue" is meant to include that portion of an amino acid that remains upon incorporation into a peptide or compound via convention amide links. For example, a glycine residue can be represented as —CO—CH$_2$—NH—. Similarly, a β-alanine residue can be represented as —CO—CH$_2$CH$_2$—NH—.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The compounds described herein are related to compounds provided in PCT publications WO 97/30677 and WO 98/05315, and to compounds provided in co-pending application Ser. No. 08/917,025 (filed Aug. 22, 1997) to application Ser. No. 60/090,681, (filed Jun. 25, 1998). More particularly, compounds are now described having an attached amino acid/peptide group.

Embodiments of the Invention

The present invention provides novel arylsulfonanilide derivatives having the formula:

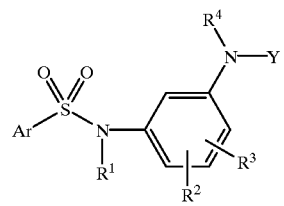

or a pharmaceutically acceptable salt thereof.

In the above formula, the letter Y represents either a linear or cyclic peptide having from four to fourteen amino acid residues or a radical of formula —Aa—Z, wherein Aa is an amino acid or dipeptide residue and Z is selected from hydrogen, —CHO,

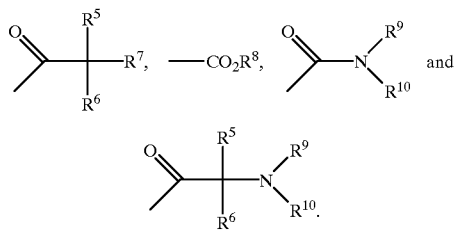

Turning first to those embodiments in which Y is a linear or cyclic peptide, preferred peptides will have from five to nine amino acid residues. A variety of amino acids are useful in the present invention, including the gene-encoded, naturally-occurring L-amino acids and their D-isomers, and non-gene encoded amino acids such as, for example, ornithine, t-butylglycine, phenylglycine, cyclohexylalanine, norleucine, 2-thienylalanine, N-methylisoleucine, homoarginine, Nα-methylarginine, sarcosine, and β-alanine. Further preferred are those embodiments in which Y represents a cyclic peptide having from five to nine amino acid residues. As used herein, the term "cyclic peptide" is meant to include those in which all of the amino acids are present in the cyclic portion, and those in which only a portion of the amino acids form a ring. Additionally, the ring or cyclic portion can be formed via disulfide linkages between cysteine residues in the peptide, or by more amide bond formation. In the latter group of embodiments, the cyclic peptide can be joined to the remainder of the molecule via a carboxylic acid group which is either present in the non-cyclized portion of the peptide, or via a carboxylic acid residue which is part of an amino acid side chain (e.g., aspartic acid or glutamic acid). The term "linear or cyclic peptide" is also meant to include those peptides in which the N-terminus is capped with an acyl group such as, for example, acetyl, pivaloyl, t-butoxycarbonyl, benzyloxycarbonyl, and the like. Particularly preferred cyclic peptides are the pentapeptides -Cys-Arg-Gly-Asn-Cys-NHAc SEQ ID NO:1 and -Cys-Arg-Gly-Asp-Cys-NHAc SEQ ID NO:2 in which a disulfide link joins the two cysteine residues. Another particularly preferred cyclic peptide is the nonapeptide -Cys-Asp-Cys-Arg-Gly-Asp-Cys-Phe-Cys-NHAc SEQ ID NO:6 in which a dissulfide link joins Cys1 to Cys7 or Cys9, or Cys3 to Cys7 or Cys9.

For those embodiments in which Y represents —Aa—Z and Z is one of the radicals above, the symbols $R^5$, $R^6$ and $R^7$ are each independently hydrogen, $(C_1-C_8)$alkyl, $(C_1-C_8)$ heteroalkyl, aryl, heteroaryl, aryl$(C_1-C_4)$alkyl, aryl$(C_1-C_4)$ heteroalkyl, heteroaryl$(C_1-C_4)$alkyl and heteroaryl$(C_1-C_4)$ heteroalkyl. Optionally, $R^5$ and $R^6$ are linked together to form a 5- or 6-membered ring. The symbol $R^8$ represents $(C_1-C_8)$alkyl, $(C_1-C_8)$heteroalkyl, aryl$(C_1-C_4)$alkyl or aryl $(C_1-C_4)$heteroalkyl. The symbols $R^9$ and $R^{10}$ are independently hydrogen, $(C_1-C_8)$alkyl, $(C_1-C_8)$heteroalkyl, aryl $(C_1-C_4)$alkyl and aryl$(C_1-C_4)$heteroalkyl, and are optionally linked together to form a 5- or 6-membered ring.

In one group of embodiments, Y represents

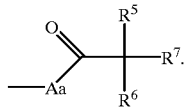

Preferred amino acid and residues (Aa) are those derived from glycine, serine, threonine, aspartic acid, β-alanine, alanine, histidine and arginine, with amino acid residues from glycine, serine and threonine being the most preferred. Also preferred are those embodiments in which Aa is a dipeptide residue derived from Ser-Gly, Thr-Gly, Gly-Ser, and Gly-Thr. Still further preferred are those embodiments in which $R^5$, $R^6$ and $R^7$ are each independently hydrogen, $(C_1-C_8)$alkyl, $(C_1-C_8)$heteroalkyl, aryl, aryl$(C_1-C_4)$alkyl, or aryl$(C_1-C_4)$heteroalkyl. Most preferred are those embodients in which $R^5$ and $R^6$ are hydrogen and $R^7$ is selected from hydrogen, $(C_1-C_8)$alkyl, aryl, or aryl$(C_1-C_4)$alkyl.

In another group of embodiments, Y represents —Aa— $CO_2R^8$. In this group of embodiments, preferred amino acid and dipeptide residues are derived from glycine, serine, threonine, aspartic acid, β-alanine, alanine, histidine, arginine, Ser-Gly, Thr-Gly, Gly-Ser and Gly-Thr. Capping the N-terminus of the amino acid and dipeptide residues is —$CO_2R^8$. Preferably, $R^8$ is $(C_1-C_8)$alkyl or aryl$(C_1-C_4)$ alkyl. More preferably, $R^8$ is methyl, ethyl, isopropyl, propyl, t-butyl, isobutyl, benzyl or 2-phenylethyl.

In still another group of embodiments, Y is

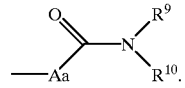

Preferred amino acid and dipeptide residues are those that have been described above. $R^9$ and $R^{10}$ are selected to provide a stable urea with the N-terminal amino group of Aa. Accordingly, $R^9$ and $R^{10}$ are independently selected from hydrogen, $(C_1-C_8)$alkyl, $(C_1-C_8)$heteroalkyl, aryl$(C_1-C_4)$ alkyl and aryl$(C_1-C_4)$heteroalkyl, and are optionally linked together to form a 5- or 6-membered ring. Preferably, $R^9$ and $R^{10}$ are hydrogen, $(C_1-C_8)$alkyl, or aryl$(C_1-C_4)$alkyl, more preferably, hydrogen, methyl, ethyl, or benzyl. Optionally, $R^9$ and $R^{10}$ are combined, with the nitrogen atom to which each is attached, to form a 5- or 6-membered ring such as, for example, a pyrrolidine, piperidine, pyridazine or morpholine ring.

In yet another group of embodiments, Y is

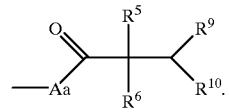

Preferred amino acid and dipeptide residues have been described above. Preferred groups for $R^5$ and $R^6$ include hydrogen, $(C_1-C_8)$alkyl, $(C_1-C_8)$heteroalkyl, aryl, aryl $(C_1-C_4)$alkyl, or aryl$(C_1-C_4)$heteroalkyl. Still further preferred are those embodiments in which $R^5$ is hydrogen and $R^6$ is hydrogen, $(C_1-C_8)$alkyl, $(C_1-C_8)$heteroalkyl, or aryl $(C_1-C_4)$alkyl. In further preferred embodiments, the alkyl groups are optionally substituted with, for example, —OH, —SH, —$CO_2H$, —$CONH_2$, —$NH_2$, —$OCH_3$, =O, or —NHC(=NH)—$NH_2$. Preferred groups for $R^9$ and $R^{10}$ are hydrogen, $(C_1-C_8)$alkyl, or aryl$(C_1-C_4)$alkyl, more preferably, hydrogen, methyl, ethyl, acetyl, propionyl, benzoyl or benzyl. As above, in certain embodiments, $R^9$ and $R^{10}$ are combined, with the nitrogen atom to which each is attached, to form a 5- or 6-membered ring.

Returning to the general formula I, above, the symbols $R^1$ and $R^4$ are each independently hydrogen, $(C_1-C_6)$alkyl or $(C_1-C_6)$heteroalkyl. Preferably, $R^1$ and $R^4$ are each independently hydrogen or $(C_1-C_4)$alkyl. More preferably, $R^1$ and $R^4$ are both hydrogen.

The symbols $R^2$ and $R^3$ independently represent hydrogen, halogen, $(C_1-C_8)$alkyl, $(C_1-C_8)$heteroalkyl, —$OR^{11}$, —$SR^{11}$ or —$NR^{11}R^{12}$, wherein $R^{11}$ and $R^{12}$ are each independently hydrogen, $(C_1-C_8)$alkyl and $(C_1-C_8)$ heteroalkyl. When $R^2$ and $R^3$ are attached to adjacent carbon atoms, they are optionally linked together to form a fused 5-, 6- or 7-membered ring. In one group of preferred embodiments, $R^2$ and $R^3$ are attached to adjacent carbon atoms C3 and C4 (relative to C1 which bears the sulfonamido group, and C5 which bears —N($R^4$)Y). In other preferred embodiments, $R^2$ is selected from hydrogen, $(C_1-C_3)$alkyl, $(C_1-C_3)$alkoxy and $(C_1-C_3)$thioalkoxy. In still other preferred embodiments, $R^3$ is selected from hydrogen, $(C_1-C_3)$alkyl, —$OR^{11}$, —$SR^{11}$ and —$NR^{11}R^{12}$ wherein $R^{11}$ and $R^{12}$ are each independently hydrogen, $(C_1-C_3)$alkyl and $(C_1-C_3)$heteroalkyl.

The symbol Ar represents a substituted aryl group selected from

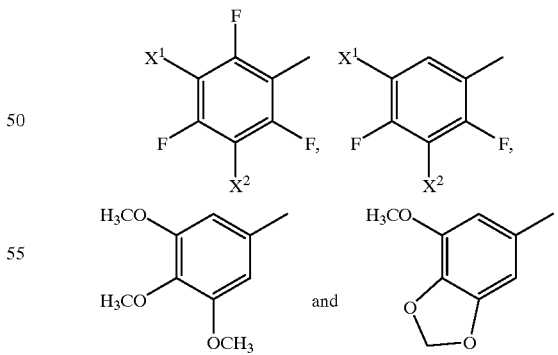

in which $X^1$ and $X^2$ are each independently F, Cl or Br. In one group of preferred embodiments, Ar is pentafluorophenyl. In another group of preferred embodiments, Ar is 2,3,4,5-tetrafluorophenyl. In yet another group of preferred embodiments, Ar is 3,4,5-trimethoxyphenyl. In still another group of preferred embodiments, Ar is 3-methoxy4,5-methylenedioxyphenyl.

Certain combinations of the above preferred embodiments are particularly preferred. In a first group of preferred embodiments, the compounds have the formula:

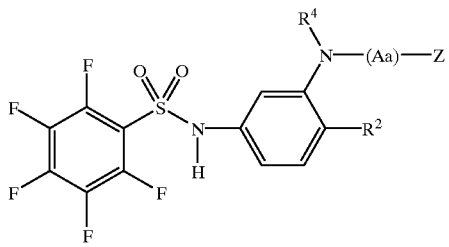

Ia

In this group of embodiments, $R^2$ is preferably hydrogen, $(C_1–C_3)$alkyl, $(C_1–C_3)$alkoxy or $(C_1–C_3)$thioalkoxy, more preferably, methyl, methoxy, ethoxy or thiomethoxy. $R^4$ is preferably hydrogen or $(C_1–C_4)$alkyl, more preferably hydrogen or methyl. Aa is preferably Gly, Ser, Thr, Asp, Ala, β-Ala, His, Arg, Ser-Gly, Gly-Ser, Thr-Gly, or Gly-Thr, most preferably Gly, L-Ser, D-Ser, L-Thr or D-Thr. Z is preferably hydrogen, acetyl, benzyloxycarbonyl, t-butyloxycarbonyl, trifluoroacetyl, N,N-dimethylcarbamoyl, N-methylcarbamoyl or carbamoyl.

In another preferred combination, the compounds have the formula:

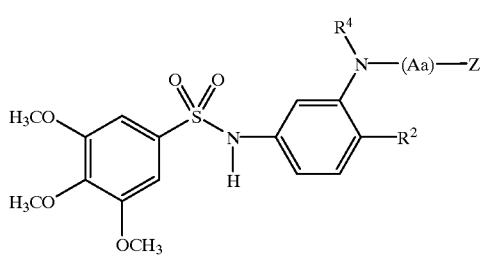

Ib

In this group of embodiments, preferred groups for $R^2$, $R^4$, Aa and Z are those that have been described for formula Ia.

Yet another group of particularly preferred embodiments is represented by formula Ic:

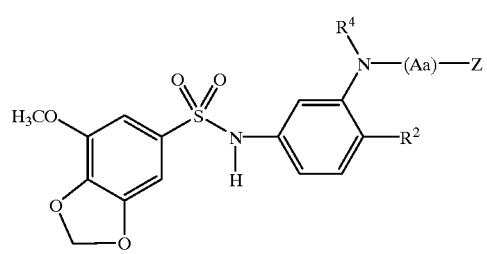

Ic

Preferred groups for $R^2$, $R^4$, Aa and Z are those that have been described for formula Ia.

Still another group of preferred embodiments are represented by formula Id.

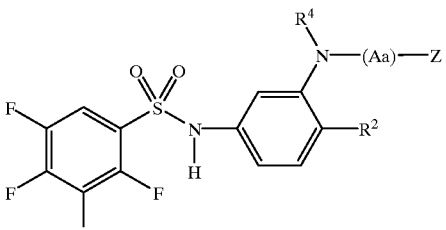

Id

Preferred groups for $R^2$, $R^4$, Aa and Z are again those that have been described for formula Ia.

Synthesis

Compounds of the present invention can be prepared using certain intermediates and methods described in WO 97/30677 and WO 98/05315. In one group of embodiments, arylsulfonamidoanilines can be prepared as described, and the anilino amino group can then be acylated with an appropriate amino acid or peptide derivative using traditional amide bond formation reactions. For example, 2-methoxy-5-pentafluorophenylsulfonamidoaniline can be treated with a suitably protected amino acid (e.g., N-α-BOC-O-benzyl-L-serine, N-BOC-glycine, N-acetyl-glycine, N-BOC-L-aspartic acid α-$^t$butyl ester, N-BOC-β-alanine, N-BOC-D-alanine, N-acetyl-L-histidine, and the like) in the presence of such coupling agents as HOBT and HBTU to form compounds of the present invention. In a similar manner, additional compounds can be formed beginning with the appropriate aniline derivative.

Following coupling of the amino acid or peptide to the sulfonamidoaniline fragment, the amino group of the amino acid or peptide portion can be further derivatized to provide, for example, a carbamate, amide or urea terminus. Procedures useful to conduct these transformations are well known in the synthesis literature for peptide derivatization. For example, treatment of the amino group with an appropriate isocyanate produces urea terminus. Similarly, treatment of the amino group with a carboxylic acid (acetic acid, propionic acid, benzoic acid, and the like) under standard acylation conditions provides an amide terminus. Alternatively, the amino acid or peptide used in preparing the compounds of the present invention can be suitably derivatized prior to coupling to the sulfonamidoaniline.

The compounds used as initial starting materials in this invention may be purchased from commercial sources or alternatively are readily synthesized by standard procedures which are well know to those of ordinary skill in the art.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3H$ (tritium) and $^{14}C$ (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

Representative compounds and compositions were demonstrated to have pharmacological activity in in vitro assays, e.g., they are capable of specifically modulating a cellular physiology to reduce an associated pathology or provide or enhance a prophylaxis.

Certain preferred compounds and compositions are capable of specifically regulating LDL receptor gene expression. Compounds may be evaluated in vitro for their ability to increase LDL receptor expression using western-blot analysis, for example, as described in Tam et al. (*J. Biol. Chem.* 1991, 266, 16764). Established animal models to evaluate hypocholesterolemic effects of compounds are known in the art. See, for example, Spady et al., *J. Clin. Invest.* 1988, 81, 300, Evans et al., *J. Lipid Res.* 1994, 35, 1634 and Lin et al., *J. Med. Chem.* 1995, 38, 277.

Certain preferred compounds and compositions display specific toxicity to various types of cells. Certain compounds and compositions of the present invention exert their cytotoxic effects by interacting with cellular tubulin. For certain preferred compounds and compositions of the present invention, that interaction is covalent and irreversible. Other compounds bind in a non-covalent manner. Compounds and compositions may be evaluated in vitro for their ability to inhibit cell growth, for example, as described in Ahmed et al., *J. Immunol. Methods* 1994, 170, 211. Established animal models to evaluate antiproliferative effects of compounds are also known in the art. For example, compounds can be evaluated for their ability to inhibit the growth of human tumors grafted into immunodeficient mice using methodology similar to that described by Rygaard and Povlsen, *Acta Pathol. Microbiol. Scand.* 1969, 77, 758, and Giovanella and Fogh, *Adv. Cancer Res.* 1985, 44, 69.

Formulation and Administration of Compounds and Pharmaceutical Compositions

The present invention provides methods of using the subject compounds and compositions to treat disease or provide medicinal prophylaxis, to slow down and/or reduce the growth of tumors, to upregulate LDL receptor gene expression in a cell, or to reduce blood cholesterol concentration in a host, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally or intravenously in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic or antiproliferative therapeutic or prophylactic agents, different from the subject compounds. In many instances, administration in conjunction with the subject compositions enhances the efficacy of such agents. Examplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES

$^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant (s) in Hertz and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses).

Examples 1, 2, 3, 17, 24, 25 and 26 provide the synthesis of certain useful intermediates. The remaining examples provide the preparation of pentafluorophenylsulfonamidoanilino amino acids and peptides. One of skill in the art will appreciate that similar reaction schemes can be used to prepare the corresponding 2,3,4,5-tetrafluorophenylsulfonamido derivatives, as well as 3,4,5-trimethoxyphenylsulfonamido and 3-methoxy-4,5-methylenedioxyphenylsulfonamido compounds.

Preparation of the starting anilines for each of those series can be produced by reduction of the corresponding nitro-containing sulfonanilide compounds, as illustrated in Example 3. These nitro compounds are obtained by reaction of the appropriate arylsulfonyl chlorides (described in co-pending applications Ser. Nos. 08/917,025 and 08/896,827) with the appropriate nitroanilines (which are illustrated herein, or known in the chemical literature).

Certain reagents are referred to by their accepted abbreviations in the Examples: N-hydroxybenzotriazole (HOBT); 2-(1H-benzotriazole-1-yl)-1,1,3,3-tetramethyluronium hexafluorophosphate (HBTU); N-methylmorpholine (NMM); 1-hydroxy-7-azabenzotriazole (HOAT); and O-(7-azabenzotriazole-1-yl)-N,N,N',N'-tetramethyluronium hexafluorophosphate (HATU).

Example 1

This example illustrates the preparation of intermediate 4-methoxy-3-nitroaniline.

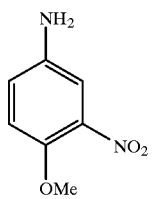

1

4-Methoxy-3-nitroaniline

To a 1M solution of 3-nitro-4-fluoroaniline (16.7 g, 107 mmol, from Aldrich Chemical Co., Milwaukee, Wis. USA) in anhydrous methanol at ambient temperature was added sodium methoxide (23.1 g, 428 mmol) and the resulting solution was refluxed with stirring for 21 hours. The reaction mixture was then cooled to 0° C. and a 12M solution of HCl (13.4 mL) was added dropwise followed by water (250 mL). The crude mixture was extracted three times with Et$_2$O (200 mL). The organic layers were combined, washed with brine (300 mL), dried over Na$_2$SO$_4$, and concentrated under vacuum to yield 17.5 g (97%) of product as a dark brown solid, which was used without further purification. $^1$H NMR (400 MHz, DMSO-d$_6$) δ7.09 (d, J=9 Hz, 1H), 7.01 (dd, J=2.8, 1.3 Hz, 1H), 6.85 (ddd, J=9, 2.8, 1.4 Hz, 1H), 5.2 (s, 2H), 3.75 (s, 3H).

Example 2

This example illustrates the synthesis of intermediate 2-nitro-4-pentafluorophenylsulfonamidoanisole.

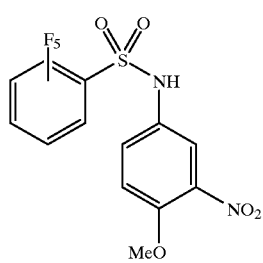

2

2-Nitro-4-pentafluorophenylsulfonamidoanisole

To a 0.4M solution of 4-methoxy-3-nitroaniline (17.5 g, 104 mmol, prepared in Example 1), in anhydrous methanol was added dropwise pentafluorophenylsulfonyl chloride (7.7 mL, 52 mmol, from Aldrich Chemical Co.) and the resulting mixture was stirred at ambient temperature for 1 hour. The reaction mixture was concentrated under vacuum and purified by column chromatography (10–30% EtOAc in hexane) to yield 18.1 g (87%) of the title compound as an orange solid, mp 95–97° C. $^1$H NMR (400 MHz, CDCl$_3$) δ7.64 (d, J=2.7 Hz, 1H), 7.51 (dd, J=9, 2.7 Hz, 1H), 7.09 (d, J=9.0 Hz, 1H), 3.95 (s, 3H). MS (EI): m/z 817 (30, 2M+Na−2H), 398 (30, M+), 397 (100, M−H).

Example 3

This example illustrates the preparation of intermediate 2-methoxy-5-pentafluorophenylsulfonamidoaniline.

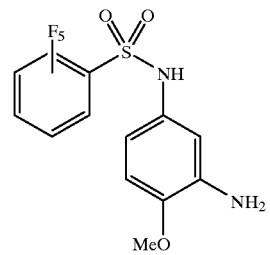

3

2-methoxy-5-pentafluorophenylsulfonamidoaniline

To a 0.15M solution of 2-nitro-4-pentafluorophenylsulfonamidoanisole (18.1 g, 45.5 mmol, prepared in Example 2), in 100% anhydrous ethanol was added 10% Pd/C (4.84 g, 4.55 mmol). Hydrogen gas was bubbled through the solution for 1 min and the resulting mixture was stirred for 24 h under 1 atmosphere of hydrogen. The crude reaction mixture was filtered through a pad of Celite and the filter pad was washed with ethanol (500 mL). The filtrate and wash were combined and concentrated under vacuum to yield 16.5 g (99%) of product as an off white solid which was used without further purification, mp 142–143° C. $^1$H NMR (400 MHz, DMSO-d$_6$) δ10.64 (s, 1H), 6.68 (d, J=8.4 Hz, 1H), 6.44 (d, J=2.1 Hz, 1H), 6.3 (dd, J=8.4, 2.1 Hz, 1H), 4.88 (bs, 2H), 3.69 (s, 3H). MS(EI): m/z 369 (100, M+H).

Example 4

This example illustrates the prepartation of a protected serine derivative of 2-methoxy-5-pentafluorophenylsulfonamidoaniline.

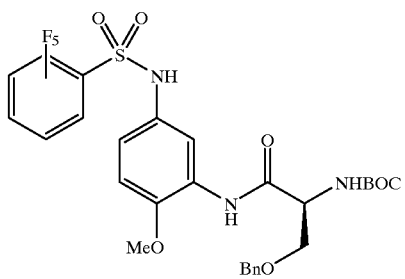

4

To 2-methoxy-5-pentafluorophenylsulfonamidoaniline (203 mg, 0.55 mmol, prepared in Example 3) was added N-t-BOC-O-benzyl-L-serine (195 mg, 0.66 mmol, from BACHEM Bioscience Inc., King of Prussia, Pa., USA), HOBT (89 mg, 0.66 mmol), and HBTU (250 mg, 0.66 mmol). DMF (3 mL) was then added, followed by NMM (60 mL, 0.55 mmol) and the resulting mixture was heated to 65° C. with stirring for 18 hours. TLC analysis showed unconsumed starting material so an additional 0.66 mmol of N-t-BOC-O-benzyl-L-serine, HOBT, HBTU, and NMM were added and the reaction mixture was stirred for an additional 10 hours. The crude reaction mixture was cooled, followed by addition of 1M solution of HCl (30 mL) and EtOAc (20 mL). The aqueous phase was extracted three times with EtOAc (20 mL). The organic phase was washed with brine (30 mL), dried over $Na_2SO_4$, and concentrated under vacuum. The crude oil was purified by column chromatography (10–50% EtOAc in hexane) to yield 267 mg (75%) of product as a pale yellow solid, mp 142–143° C. $^1$H NMR (400 MHz, DMSO-$d_6$) δ10.9 (s, 1H), 9.1 (s, 1H), 7.98 (s, 1H), 7.4–7.2 (m, 6H), 7.0 (d, J=8.5 Hz, 1H), 6.9 (dd, J=8.5, 2.6 Hz, 4.5 (s, 2H), 4.2 (bs, 2H), 3.79 (s, 3H), 3.65–3.6 (m, 2H), 1.4 (s, 9H). MS(EI): m/z 645 (35, M+), 644.2 (100, M–H).

Example 5

This example illustrates the preparation of a serine derivative of 2-methoxy-5-pentafluorophenylsulfonamidoaniline via removal of the protecting groups present in compound 4.

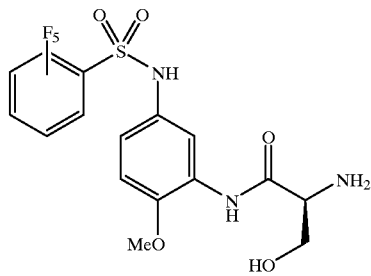

5

To a 0.08M solution of compound 4 prepared in Example 4 (267 mg, 0.41 mmol) in $CH_2Cl_2$ at 0° C. was added trifluoroacetic acid (TFA, 2.5 mL, 32.7 mmol) and the resulting solution was stirred for 19 h as ambient temperature was reached. The crude reaction mixture was concentrated under vacuum with azeotropic removal of TFA using hexane and purified by column chromatography (1–5% MeOH in $CH_2Cl_2$) to yield 225 mg (100%) of the free amino product. To a 0.01M solution of this intermediate (127 mg, 0.23 mmol) in glacial acetic acid was added 20% palladium hydroxide (245 mg, 0.23 mmol). Hydrogen gas was bubbled through the solution for 1 min. and the resulting mixture was stirred for 17 h under 1 atmosphere of hydrogen gas. The crude reaction was filtered through a pad of celite, the celite was washed with ethanol (100 mL) and the filtrate was concentrated under vacuum with azeotropic removal of acetic acid using hexane. Purification by column chromatography (1–10% MeOH in $CH_2Cl_2$) yielded 42 mg (40%) of product as a white solid, mp 65° C. $^1$H NMR (400 MHz, DMSO-$d_6$) δ9.9 (s, 1H), 7.95 (s, 1H), 6.92 (d, J=8.5 Hz, 1H), 6.8 (d, J=8.6 Hz, 1H), 5.1 (bs, 1H), 3.79 (s, 3H), 3.7–3.5 (m, 3H). MS(EI): m/z 478 (20, M+Na), 456 (100, M+H).

Example 6

This example illustrates acetylation of compound 5 to form compound 6.

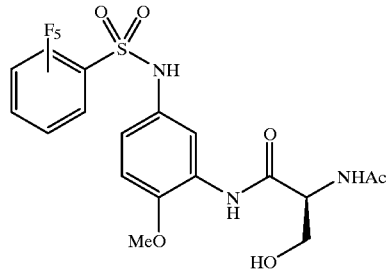

6

To a 0.06M solution of compound 5 (prepared in Example 5, 88 mg, 0.19 mmol) in $CH_2Cl_2$ at 0° C., was added pyridine (31 mL, 0.39 mmol) followed by acetic anhydride (20 mL, 0.21 mmol). The ice bath was removed and the reaction mixture was stirred for 1.5 hours. EtOAc (15 mL) and a 1M solution of HCl (15 mL) were added and the aqueous layer was extracted twice with EtOAc (15 mL). The organic layers were combined and washed once with brine (30 mL), dried over $Na_2SO_4$, concentrated under vacuum and purified by column chromatography (1–5% MeOH in $CH_2Cl_2$) to yield 74 mg (77%) of product as a white solid, mp 98–99° C. $^1$H NMR (400 MHz, DMSO-$d_6$) δ10.9 (s, 1H), 9.09 (s, 1H), 8.2 (d, J=7.3 Hz, 1H), 7.99 (d, J=2.2 Hz, 1H), 7.0 (d, J=8.6 Hz, 1H), 6.88 (dd, J=8.7, 2.6 Hz, 1H), 5.1 (t, J=5.1 Hz, 1H), 4.4 (apparent q, J=6.1 Hz, 1H), 3.8 (s, 3H), 3.7–3.55 (m, 2H), 1.9 (s, 3H).). MS(EI): m/z 497 (20, M+), 496 (100, M–H). or alternatively To 2-methoxy-5-pentafluorophenylsulfonamidoaniline, prepared in Example 3, (500 mg, 1.36 mmol) was added N-acetyl-O-$^t$butyl-L-serine (360 mg, 1.77 mmol), HBTU (671 mg, 1.77 mmol), and HOBT (239 mg, 1.77 mmol). To the resulting mixture was added DMF (7.6 mL) followed by NMM (0.15 mL, 1.36 mmol) and the reaction mixture was stirred for 22 h at 65° C. The crude reaction was cooled to ambient temperature followed by addition of a 1M solution of HCl (30 mL) and EtOAc (20 mL). The aqueous phase was extracted three times with EtOAc (30 mL). The organic layers were combined and washed once with brine (20 mL), dried over $Na_2SO_4$, and concentrated under vacuum. The crude material was purified by column chromatography (1–5% MeOH in $CH_2Cl_2$) to yield 700 mg (93%) of product as an orange solid which was dissolved in $CH_2Cl_2$ (8.5 mL) and cooled to 0° C. TFA (8 mL, 100 mmol) was then added and the solution was stirred for 8.5 h at 0° C. The reaction was cooled to −26° C. for 12 hr and then warmed to ambient temperature for an additional 5 hr with stirring. The crude reaction was concentrated under vacuum with azeotropic removal of TFA with hexane and purified by column chromatography (1–5% MeOH in $CH_2Cl_2$) followed by HPLC chromatography (5–95% $CH_3CN$ in $H_2O$) over 30 min to yield 457 mg (73%) of product 6 as a white solid.

Example 7

This example illustrates the prepartation of a protected glycine derivative of 2-methoxy-5-pentafluorophenylsulfonamidoaniline.

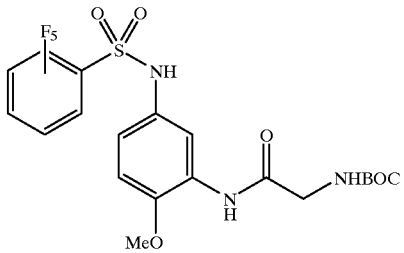

7

Sulfonamide 7 was synthesized in a similar manner to that described for compound 4 in Example 4. mp 204–205° C., $^1$H NMR (400 MHz, DMSO-$d_6$) δ10.9 (s, 1H), 9.0 (s, 1H), 7.25 (bs, 1H), 7.0 (d, J=9.5 Hz, 1H), 6.89 (dd, J=8.9, 2.6 Hz, 1H), 3.8 (s, 3H), 3.69 (d, J=5.5 Hz, 2H), 1.39 (s, 9H). MS(EI): m/z 525 (25, M+), 542 (100, M−H).

Example 8

This example illustrates the preparation of a glycine derivative of 2-methoxy-5-pentafluorophenylsulfonamidoaniline via removal of the protecting group present in compound 7.

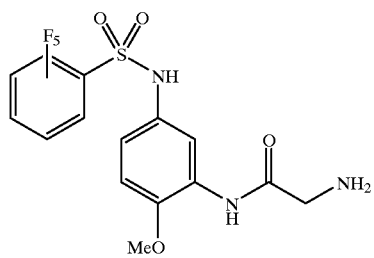

8

Compound 8 was synthesized from compound 7 using a BOC removal procedure similar to that of Example 5. MS(EI): m/z 448 (15, M+Na), 426 (25, M+H), 369 (100).

Example 9

This example illustrates the preparation of a N-acetyl-glycine derivative of 2-methoxy-5-pentafluorophenylsulfonamidoaniline.

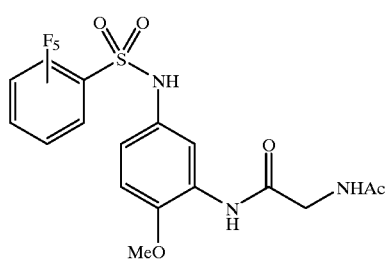

9

Compound 9 was synthesized from 2-methoxy-5-pentafluorophenylsulfonamidoaniline and N-acetyl-glycine using a procedure similar to that of Example 4. mp 209–210° C. $^1$H NMR (400 MHz, DMSO-$d_6$) δ10.9 (s, 1H), 9.1 (s, 1H), 8.29 (t, J=5.7 Hz, 1H), 7.88 (s, 1H), 6.99 (d, J=8.9 Hz, 1H), 6.88 (dd, J=8.8, 2.6 Hz, 1H), 3.85 (d, J=5.9 Hz, 2H), 3.79 (s, 3H), 1.89 (s, 3H). MS(EI): m/z 467 (20, M+), 466 (100, M−H).

Example 10

This example illustrates the preparation of a N-acetyl-threonine derivative of 2-methoxy-5-pentafluorophenylsulfonamidoaniline.

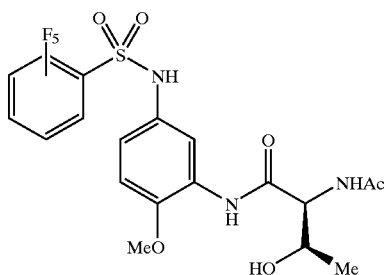

10

Compound 10 was synthesized from 2-methoxy-5-pentafluorophenylsulfonamidoaniline and N-BOC-O-benzyl-L-threonine using a procedure similar to that of Examples 4, 5, and 6. $^1$H NMR (400 MHz, DMSO-$d_6$) δ10.9 (s, 1H), 9.1 (s, 1H), 8.05 (d, J=8.3 Hz, 1H), 7.99 (d, J=2.5 Hz, 1H), 7.0 (d, J=8.8 Hz, 1H), 6.86 (dd, J=8.8, 2.6 Hz, 1H), 5.2 (d, J=4.8 Hz, 1H), 4.39 (dd, J=8.1, 3.6 Hz, 1H), 4.1–4.0 (m, 1H), 3.8 (s, 3H), 1.95 (s, 3H), 1.08 (d, J=6.3 Hz, 3H). MS(EI): m/z 511 (20, M+), 510 (100, M−H).

Example 11

This example illustrates the prepartation of an aspartic acid derivative of 2-methoxy-5-pentafluorophenylsulfonamidoaniline.

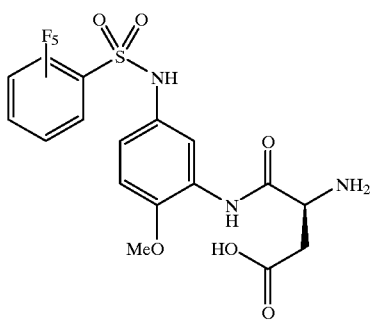

11

Compound 11 was synthesized from 2-methoxy-5-pentafluorophenylsulfonamidoaniline and N-BOC-L-aspartic acid α-$^t$butyl ester using a procedure similar to that of Examples 4 and 5. mp 170–172° C., $^1$H NMR (400 MHz, DMSO-$d_6$) δ10.99 (s, 1H), 9.8 (s, 1H), 8.22 (bs, 2H), 7.9 (d, J=2.5 Hz, 1H), 7.04 (d, J=8.9 Hz, 1H), 6.91 (dd, J=8.8, 2.6 Hz, 1H), 4.1 (bs, 1H), 3.8 (s, 3H), 2.89 (dd, J=17.9, 5.1 Hz, 1H), 2.78 (dd, J=17.9, 7.6 Hz, 1H). MS(EI): m/z 989 (15, 2M+Na), 967 (30, 2M+H), 506 (65, M+Na), 484 (100, M+H).

Example 12

This example illustrates acetylation of compound 11 to form compound 12.

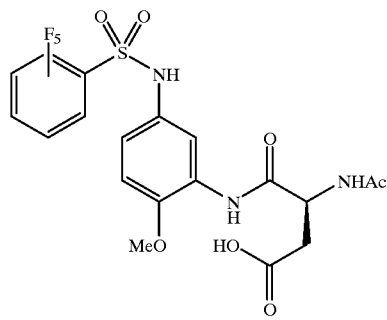

12

Compound 12 was synthesized from compound 11 using a procedure similar to that of Example 6. $^1$H NMR (400 Mhz, DMSO-d$_6$) δ12.0 (bs, 2H), 9.0 (s, 1H), 8.45 (d, J=7.4 Hz, 1H), 7.75 (s, 1H), 6.89 (d, J=8.9 Hz, 1H), 6.78 (dd, J=8.3, 1.1 Hz, 1H), 4.68 (ddd, J=7.5, 7.0, 6.4 Hz, 1H), 3.75 (s, 3H), 2.75 (dd, J=16.1, 6.4 Hz, 1H), 2.5 (dd, J=16.1, 7.0 Hz, 1H), 1.9 (s, 3H). MS(EI): m/z 1073 (15, 2M+Na), 548 (60, M+Na), 526 (15, M+H).

Example 13

This example illustrates the preparation of a N-acetyl-β-alanine derivative of 2-methoxy-5-pentafluorophenylsulfonamidoaniline.

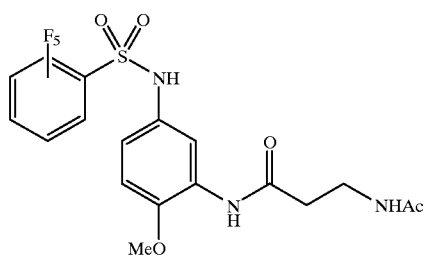

13

Compound 13 was synthesized from 2-methoxy-5-pentafluorophenylsulfonamido-aniline and N-BOC-β-alanine using procedures similar to those of Examples 4,5, and 6. mp 169–170° C., $^1$H NMR (400 MHz, DMSO-d$_6$) δ10.85 (s, 1H), 9.12 (s, 1H), (bs, 1H), 6.98 (dd, J=8.8, 2.9 Hz, 1H), 6.88 (d, J=8.7 Hz 1H), 3.79 (s, 3H), 3.4–3.2 (m, 4H), 1.78 (s, 3H). MS(EI): m/z 482 (100, M+H).

Example 14

This example illustrates the preparation of an L-alanine derivative of 2-methoxy-5-pentafluorophenylsulfonamidoaniline.

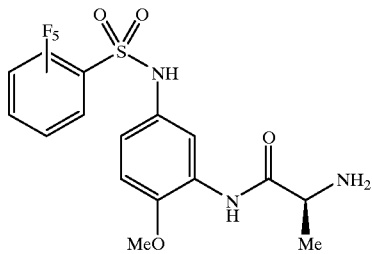

14

Compound 14 was synthesized from 2-methoxy-5-pentafluorophenylsulfonamidoaniline and N-BOC-L-alanine using procedures similar to those of Examples 4 and 5. MS(EI): m/z 440 (100, M+H).

Example 15

This example illustrates the preparation of a D-alanine derivative of 2-methoxy-5-pentafluorophenylsulfonamidoaniline.

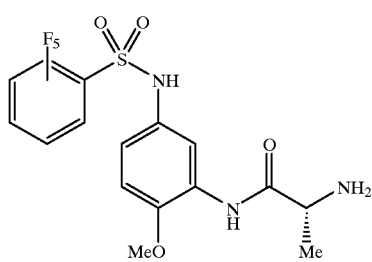

15

Compound 15 was synthesized from 2-methoxy-5-pentafluorophenylsulfonamidoaniline and N-BOC-D-alanine using procedures similar to those of Examples 4 and 5. mp 110° C. $^1$H NMR (400 MHz, DMSO-d$_6$) δ10.99 (bs, 1H), 9.75 (s, 1H), 8.1 (bs, 2H), 7.85 (s, 1H), 7.03 (d, J=8.8 Hz, 1H), 6.9 (dd, J=8.9, 2.6 Hz, 1H), 4.25–4.1 (m, 1H), 3.8 (s, 3H), 1.4 (d, J=6.9 Hz, 3H). MS(EI): m/z 440 (100, M+H).

Example 16

This example illustrates the preparation of an N-acetyl-D-alanine derivative of 2-methoxy-5-pentafluorophenylsulfonamidoaniline.

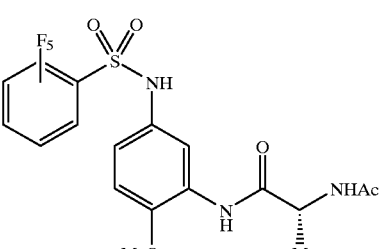

16

Compound 16 was synthesized from 2-methoxy-5-pentafluorophenylsulfonamido-aniline and N-BOC-D- alanine using procedures similar to those of Examples 4, 5 and 6. mp 189–190° C. $^1$H NMR (400 MHz, DMSO-$d_6$) δ10.89 (s, 1H), 9.1 (s, 1H), 8.28 (d, J=6.5 Hz, 1H), 7.89 (s, 1H), 7.0 (d, J=8.9 Hz, 1H), 6.88 (dd, J=8.8, 2.7 Hz, 1H), 4.55–4.35 (m, 1H), 3.8 (s, 3H), 1.85 (s, 3H), 1.23 (d, J=7.2 Hz, 3H). MS(EI): m/z 481 (25, M+), 480 (100, M–H).

Example 17

This example illustrate the preparation of intermediate 3-methylamino-4-methoxy-1-pentafluorophenylsulfonamidobenzene.

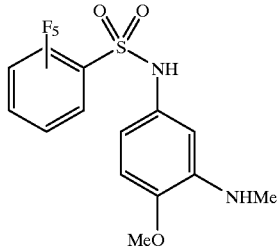

17

3-Methylamino-4-methoxy-1-pentafluorophenylsulfonamidobenzene

To a 0.5M solution of 2-formamido-4-nitroanisole (745 mg, 3.8 mmol) in dioxane was added sodium borohydride (722 mg, 19 mmol) followed by dropwise addition of glacial acetic acid (1.09 mL, 19 mmol). The reaction mixture was refluxed for 40 minutes, then cooled to 0° C. and quenched slowly with MeOH. Excess MeOH was then added and the solution was concentrated under vacuum to yield 2-methylamino-4-nitroanisole. The crude product was dissolved in anhydrous MeOH (20 mL) and Pd/C (795 mg, 0.76 mmol) was added followed by bubbling hydrogen gas through the solution for 1 minute. The reaction mixture was then stirred for 1.5 h under 1 atmosphere of hydrogen. The reaction mixture was filtered through a pad of Celite and the filter pad was washed with MeOH (40 mL). To the combined filtrate and wash was added pentafluorophenylsulfonyl chloride (282 mL, 0.26 mmol). After stirring for 30 min the reaction mixture was concentrated under vacuum and purified by column chromatography (10–25% EtoAc in hexane) to yield 153 mg (21% for three steps) of the title compound as a pale yellow solid. $^1$H NMR (400 MHz, DMSO-$d_6$) δ10.7 (s, 1H), 6.68 (d, J=8.4 Hz, 1H), 6.3 (dd, J=8.3, 2.5 Hz, 1H), 6.22 (d, J=2.2 Hz, 1H), 5.18 (bs, 1H), 3.7 (s, 3H), 2.6 (d, J=3Hz, 3H). MS(EI): m/z 785 (35, 2M+Na–2H), 382 (20, M+), 381 (100, M–H).

Example 18

This example illustrates the preparation of a N-acetylglycine derivative of 3-methylamino-4-methoxy-1-pentafluorophenylsulfonamidobenzene.

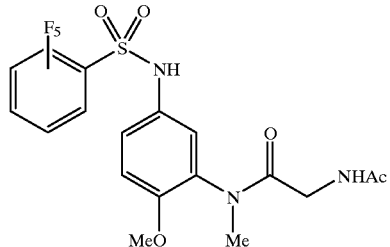

18

To a 0.18M solution of 3-N(Methyl)-4-methoxy-1-pentafluorophenylsulfonamidobenzene, prepared in example 17, (73 mg, 0.19 mmol) in DMF was added N-acetylglycine (29 mg, 0.25 mmol), HOAT (34 mg, 0.25 mmol), HATU (94 mg, 0.25 mmol), and NMM (0.021 mL, 0.19 mmol). The reaction mixture was heated to 65° C. and stirred for 24 hours. A 1M solution of HCl (30 mL) and EtOAc (30 mL) were added and the aqueous layer was extracted 3× with EtOAc (30 mL). The organic layers were combined, washed once with brine (50 mL), dried over $Na_2SO_4$, and concentrated under vacuum. The crude material was purified by column chromatography (1–3% MeOH in $CH_2Cl_2$) to yield 72 mg (78%) of the title compound 18 as a white solid. $^1$H NMR (400 MHz, DMSO-$d_6$) δ11.01 (s, 1H), 7.9 (t, J=5.4 Hz, 1H), 7.2 (dd, J=8.9, 2.2 Hz, 1H), 7.05 (d, J=2.2 Hz, 1H), 3.8 (s, 3H), 3.39 (dd, J=16.9, 5.8 Hz, 1H), 3.15 (dd, J=16.8, 5.3 Hz, 1H), 1.8 (s, 3H). MS(EI): m/z 481 (25, M+), 480 (100, M–H).

Example 19

This example illustrates the prepartation of a protected serine derivative of 3-methylamino-4-methoxy-1-pentafluorophenylsulfonamidobenzene.

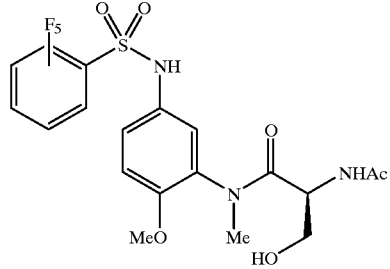

19

The title compound 19 can be prepared from 3-methylamino-4-methoxy-1-pentafluorophenylsulfonamidobenzene and N-acetyl-O-$^t$butyl-L-serine using a procedure similar to that of Example 6. MS(EI): m/z 511 (25, M+), 510 (100, M–H).

Example 20

This example illustrates the preparation of a N-acetyl-L-histidine derivative of 2-methoxy-5-pentafluorophenylsulfonamidoaniline.

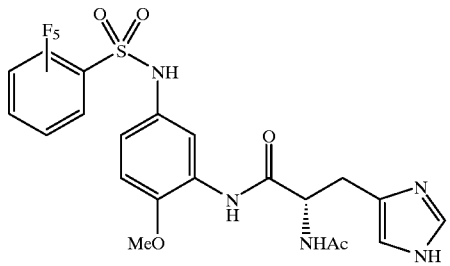

20

The title compound 20 can be synthesized from 3-amino-4-methoxy-1-pentafluorophenylsulfonamidobenzene and N-acetyl-L-histidine using a procedure similar to that of Example 6.

Example 21

This example illustrates the preparation of a N-acetyl-L-arginine derivative of 2-methoxy-5-pentafluorophenylsulfonamidoaniline.

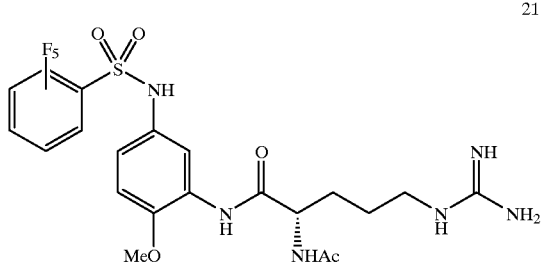

21

The title compound 21 can be synthesized from 3-amino-4-methoxy-1-pentafluorophenylsulfonamidobenzene and N-acetyl-L-arginine using a procedure similar to that of Example 6.

Example 22

This example illustrates the preparation of a di-N-acetyl-L-arginine derivative of 2-methoxy-5-pentafluorophenylsulfonamidoaniline.

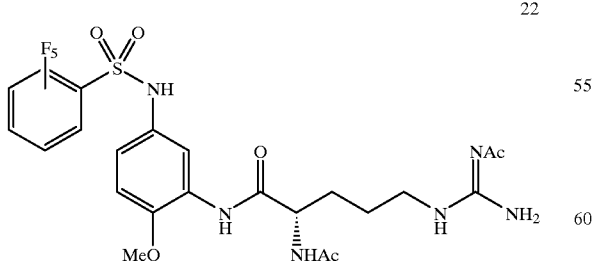

22

The title compound 22 can be synthesized from 3-amino-4-methoxy-1-pentafluorophenylsulfonamidobenzene and N-acetyl-L-arginine using a procedure similar to that of Example 6.

Example 23

This example, along with Examples 24 and 25 illustrate the preparation of intermediates which can then be derivatized with amino acid and peptide groups using the procedures described above to form compounds having N-alkyl and N-heteroalkyl groups.

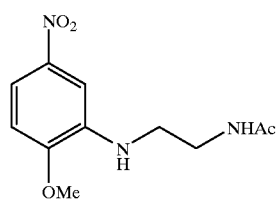

23.1

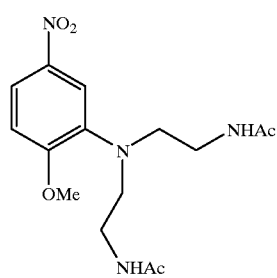

23.2

To a 0.1M solution of 2-methoxy-5-nitroaniline (1 g, 6 mmol) in an 83% aqueous AcOH solution is added aziridine (1.68 g, 39 mmol). The reaction mixture is stirred for 5 days, concentrated under vacuum, and purified by column chromatography. To the purified products is added pyridine (2 eq.) followed by acetic anhydride (1 Eq.). The crude reaction material is concentrated and purified by column chromatography to provide the title compounds.

Example 24

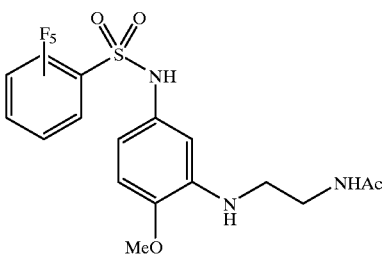

24

The title compound 24 can be synthesized form pentafluorophenylsulfonyl chloride and intermediate 23.1, using a procedure similar to that of Example 2.

Example 25

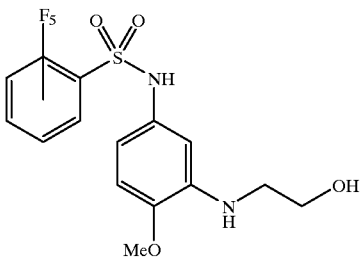

The title compound 25 can be synthesized in a similar manner as described in Examples 23 and 24 by replacing aziridine with ethylene oxide.

Example 26

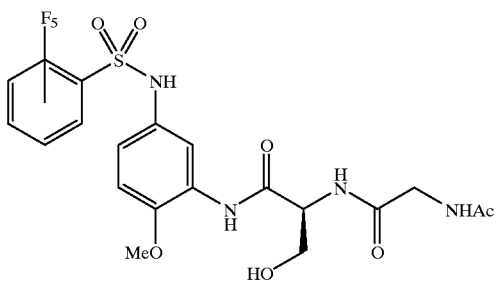

The title compound 26 can be synthesized from 3-amino-4-methoxy-1-pentafluorophenylsulfonamidobenzene, N-BOC-O$^t$Bu-L-serine, and N-acetylglycine using a procedure similar to that of Example 18.

Example 27

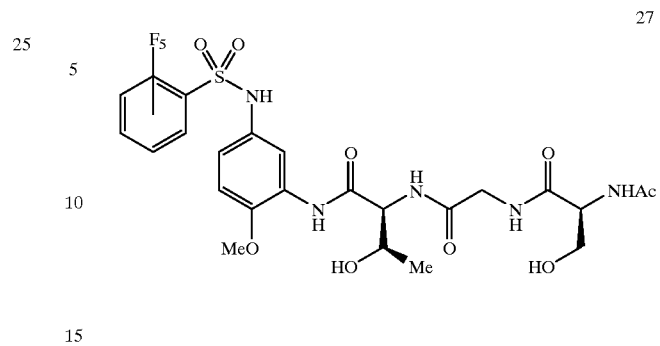

The title compound 27 can be synthesized from 3-amino-4-methoxy-1-pentafluorophenylsulfonamidobenzene, N-BOC-O$^t$Bu-L-threonine, N-BOC-glycine and, N-acetyl-O-$^t$Butyl-L-serine using a procedure similar to that of Example 18.

Example 28

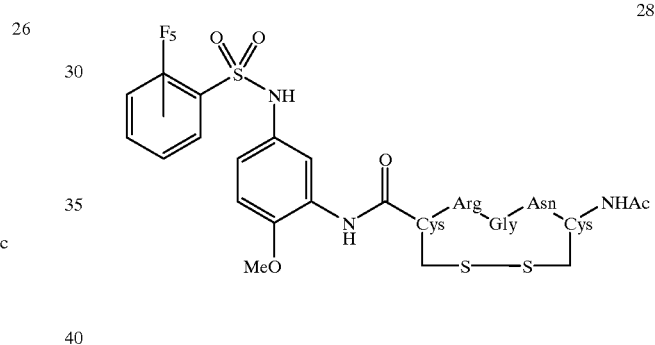

The title compound 28 (SEQ ID NO:4) can be synthesized from 3-amino-4-methoxy-1-pentafluorophenylsulfonamidobenzene and N-acetyl-CNGRC-OH (SEQ ID NO:1) cyclic pentapeptide (Arap, W.; Pasqualini, R.; Ruoslaht, E. *Science* 1998, 279, 16, 377.) using a procedure similar to that of Example 18.

Example 29

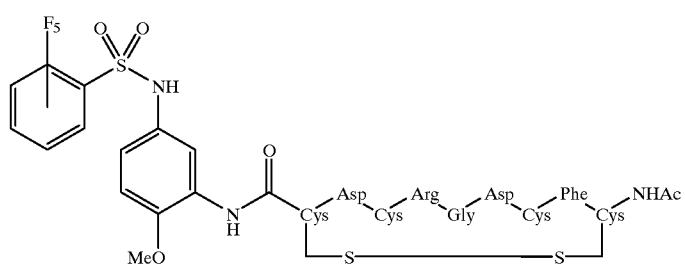

The title compound 29 (SEQ ID NO:5) can be synthesized from 3-amino-4-methoxy-1-pentafluorophenylsulfonamidobenzene and N-acetyl-CFCDGRCDC-OH (SEQ ID NO:6) cyclic nonapeptide (Arap, W.; Pasqualini, R.; Ruoslaht, E. *Science* 1998, 279, 16, 377.) using a procedure similar to that of Example 18.

Example 30
Assessment of Biological Activity.

The ability of test compounds to arrest the growth of tumor cells in culture was evaluated using HeLa cells, derived from a human cervical adenocarcinoma, and obtained from the American Type Culture Collection (ATCC, Rockville, Md.). Cells were grown in culture in the usual way. Test compounds were dosed in triplicate at concentrations ranging from 5 nM to 50 μM, and the cellular growth rate was calculated by harvesting the cells after 72 hours of treatment and measuring their metabolic activity using an Alamar Blue assay (Biosource International, Camarillo, Calif.). The degree of metabolic activity in the culture is proportional to the number of living cells. See, Ahmed et al., *J. Immunol. Methods* 1994, 170, 211. The change in growth rate for cells treated with test compounds was normalized to the growth of untreated cells and a plot of normalized cellular growth vs. compound concentration was made. The concentration at which total growth inhibition (TGI) occurred was determined and is provided in Table 1 as a micromolar concentration.

TABLE 1

| Compound | TGI ($\mu$M) |
|---|---|
| 5 | 2 |
| 6 | 0.07 |
| 8 | 10 |
| 9 | 0.07 |
| 10 | 0.07 |
| 12 | 5.5 |
| 13 | 50 |
| 14 | 5 |
| 15 | 5 |
| 16 | 2 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

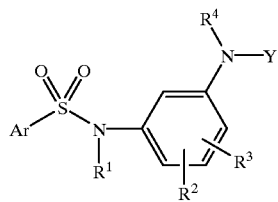

or a pharmaceutically acceptable salt thereof, wherein

Y is a linear or cyclic peptide having from four to fourteen amino acid residues, or a radical of formula —Aa—Z, wherein Aa is an amino acid or dipeptide residue and Z is a member selected from the group consisting of hydrogen, —CHO,

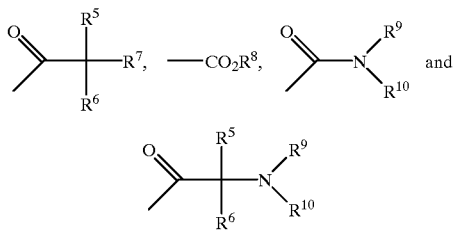

wherein $R^5$, $R^6$ and $R^7$ are each independently selected from the group consisting of hydrogen, $(C_1-C_8)$alkyl, $(C_1-C_8)$heteroalkyl, aryl, heteroaryl, aryl$(C_1-C_4)$ alkyl, aryl$(C_1-C_4)$heteroalkyl, heteroaryl$(C_1-C_4)$ alkyl and heteroaryl$(C_1-C_4)$heteroalkyl, and $R^5$ and $R^6$ are optionally linked together to form a 5- or 6-membered ring; and $R^8$ is a member selected from the group consisting of $(C_1-C_8)$alkyl, $(C_1-C_8)$heteroalkyl, aryl$(C_1-C_4)$alkyl and aryl$(C_1-C_4)$heteroalkyl;

$R^9$ and $R^{10}$ are members independently selected from the group consisting of hydrogen, $(C_1-C_8)$alkyl, $(C_1-C_8)$heteroalkyl, aryl$(C_1-C_4)$alkyl and aryl $(C_1-C_4)$heteroalkyl, and are optionally linked together to form a 5- or 6-membered ring;

$R^1$ and $R^4$ are each members independently selected from the group consisting of hydrogen, $(C_1-C_6)$alkyl and $(C_1-C_6)$heteroalkyl;

$R^2$ and $R^3$ are each independently selected from the group consisting of hydrogen, halogen, $(C_1-C_8)$alkyl, $(C_1-C_8)$heteroalkyl, —OR$^{11}$, —SR$^{11}$ and —NR$^{11}$R$^{12}$, wherein $R^{11}$ and $R^{12}$ are each independently selected from the group consisting of hydrogen, $(C_1-C_8)$alkyl and $(C_1-C_8)$heteroalkyl; and $R^2$ and $R^3$, when attached to adjacent carbon atoms, are optionally linked together to form a fused 5-, 6- or 7-membered ring; and Ar is a substituted aryl group selected from the group consisting of:

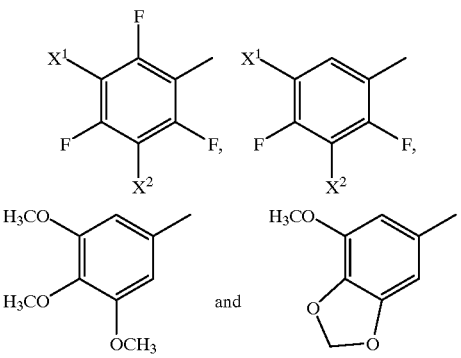

wherein $X^1$ and $X^2$ are each independently selected from the group consisting of F, Cl and Br.

2. A compound of claim 1, wherein Y is —Aa—Z.

3. A compound of claim 2, wherein Aa is an amino acid residue selected from the group consisting of Gly, L-Ser, L-Thr, D-Ser and D-Thr.

4. A compound of claim 2, wherein Aa is a dipeptide residue selected from the group consisting of Ser-Gly, Gly-Ser, Thr-Gly and Gly-Thr.

5. A compound of claim 2, wherein Z is —CO$_2$R$^8$.

6. A compound of claim 2, wherein Z is —C(O)NR$^9$R$^{10}$.

7. A compound of claim 2, wherein Z is —C(O)CR$^5$R$^6$R$^7$, and $R^5$, $R^6$ and $R^7$ are each independently selected from the group consisting of hydrogen, $(C_1-C_8)$alkyl and $(C_1-C_8)$ heteroalkyl.

8. A compound of claim 2, wherein Z is

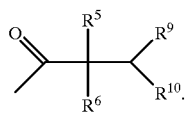

9. A compound of claim 1, wherein Ar is pentafluorophenyl.

10. A compound of claim 1, wherein Ar is 2,3,4,5-tetrafluorophenyl.

11. A compound of claim 1, wherein Ar is 3,4,5-trimethoxyphenyl.

12. A compound of claim 1, wherein Ar is 3-methoxy-4,5-methylenedioxyphenyl.

13. A compound of claim 1, wherein $R^1$ and $R^4$ are both hydrogen.

14. A compound of claim 13, wherein $R^2$ is selected from the group consisting of hydrogen, $(C_1-C_3)$alkyl and $(C_1-C_3)$alkoxy.

15. A compound of claim 13, wherein $R^3$ is selected from the group consisting of hydrogen, $(C_1-C_3)$alkyl, $-OR^{11}$ and $-NR^{11}R^{12}$, wherein $R^{11}$ and $R^{12}$ are each independently selected from the group consisting of hydrogen, $(C_1-C_3)$alkyl and $(C_1-C_3)$heteroalkyl.

16. A compound of claim 1, wherein $R^1$, $R^2$ and $R^4$ are hydrogen, and $R^3$ is located in the para-position relative to the sulfonamide moiety and is selected from the group consisting of hydrogen, fluorine, $(C_1-C_3)$alkyl, $(C_1-C_3)$alkoxy and $(C_1-C_3)$thioalkoxy.

17. A compound of claim 16, wherein Ar is pentafluorophenyl.

18. A compound of claim 16, wherein Ar is 2,3,4,5-tetrafluorophenyl.

19. A compound of claim 16, wherein Ar is 3,4,5-trimethoxyphenyl.

20. A compound of claim 16, wherein Ar is 3-methoxy-4,5-methylenedioxyphenyl.

21. A compound of claim 17, wherein Y is —Aa—Z, and Z is selected from the group consisting of hydrogen, —CHO, —C(O)CR$^5$R$^6$R$^7$ and —CO$_2$R$^8$.

22. A compound of claim 18, wherein Y is —Aa—Z, and Z is selected from the group consisting of hydrogen, —CHO, —C(O)CR$^5$R$^6$R$^7$ and —CO$_2$R$^8$.

23. A compound of claim 19, wherein Y is —Aa—Z, and Z is selected from the group consisting of hydrogen, —CHO, —C(O)CR$^5$R$^6$R$^7$ and —CO$_2$R$^8$.

24. A compound of claim 20, wherein Y is —Aa—Z, and Z is selected from the group consisting of hydrogen, —CHO, —C(O)CR$^5$R$^6$R$^7$ and —CO$_2$R$^8$.

25. A compound of claim 1, wherein Ar is pentafluorophenyl; $R^1$, $R^2$ and $R^4$ are each hydrogen; $R^3$ is 4-methoxy; and Y is —Aa—Z, wherein Aa is selected from the group consisting of glycine, L-serine, D-serine, L-threonine and D-threonine, and Z is acetyl.

26. A pharmaceutical composition comprising a pharmaceutically acceptable excipient and a compound having the formula:

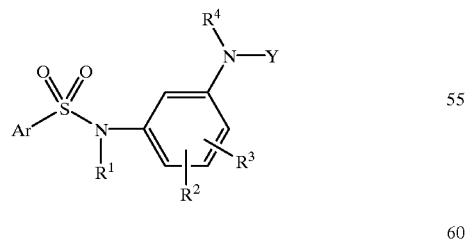

or a pharmaceutically acceptable salt thereof, wherein

Y is a linear or cyclic peptide having from four to fourteen amino acid residues, or a radical of formula —Aa—Z, wherein Aa is an amino acid or dipeptide residue and Z is a member selected from the group consisting of hydrogen, —CHO,

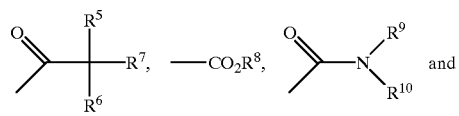

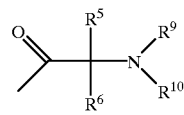

wherein $R^5$, $R^6$ and $R^7$ are each independently selected from the group consisting of hydrogen, $(C_1-C_8)$alkyl, $(C_1-C_8)$heteroalkyl, aryl, heteroaryl, aryl$(C_1-C_4)$alkyl, aryl$(C_1-C_4)$heteroalkyl, heteroaryl$(C_1-C_4)$alkyl and heteroaryl$(C_1-C_4)$heteroalkyl, and $R^5$ and $R^6$ are optionally linked together to form a 5- or 6-membered ring; and $R^8$ is a member selected from the group consisting of $(C_1-C_8)$alkyl, $(C_1-C_8)$heteroalkyl, aryl$(C_1-C_4)$alkyl and aryl$(C_1-C_4)$heteroalkyl;

$R^9$ and $R^{10}$ are members independently selected from the group consisting of hydrogen, $(C_1-C_8)$alkyl, $(C_1-C_8)$heteroalkyl, aryl$(C_1-C_4)$alkyl and aryl$(C_1-C_4)$heteroalkyl, and are optionally linked together to form a 5- or 6-membered ring;

$R^1$ and $R^4$ are each members independently selected from the group consisting of hydrogen, $(C_1-C_6)$alkyl and $(C_1-C_6)$heteroalkyl;

$R^2$ and $R^3$ are each independently selected from the group consisting of hydrogen, halogen, $(C_1-C_8)$alkyl, $(C_1-C_8)$heteroalkyl, $-OR^{11}$, $-SR^{11}$ and $-NR^{11}R^{12}$, wherein $R^{11}$ and $R^{12}$ are each independently selected from the group consisting of hydrogen, $(C_1-C_8)$alkyl and $(C_1-C_8)$heteroalkyl; and $R^2$ and $R^3$, when attached to adjacent carbon atoms, are optionally linked together to form a fused 5-, 6- or 7-membered ring; and Ar is a substituted aryl group selected from the group consisting of:

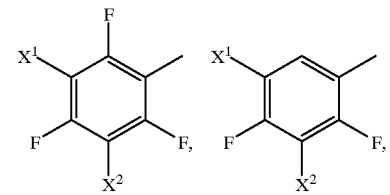

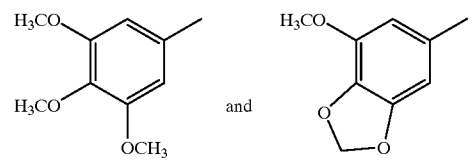

wherein $X^1$ and $X^2$ are each independently selected from the group consisting of F, Cl and Br.

27. A composition of claim 26, wherein Ar is selected from the group consisting of

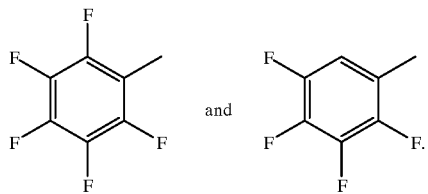

28. A composition of claim 26, wherein Ar is pentafluorophenyl.

29. A composition of claim 26, wherein Ar is 2,3,4,5-tetrafluorophenyl.

30. A composition of claim 26, wherein Ar is 3,4,5-trimethoxylphenyl.

31. A composition of claim 26, wherein Ar is 3-methoxy-4,5-methylenedioxyphenyl.

32. A composition of claim 26, wherein Y is a linear or cyclic peptide having from four to fourteen amino acid residues.

33. A composition of claim 26, wherein Y is a cyclic pentapeptide.

34. A composition of claim 26, wherein Y is a cyclic nonapeptide.

35. A composition of claim 28, wherein $R^1$ and $R^4$ are both hydrogen.

36. A composition of claim 28, wherein $R^2$ is selected from the group consisting of hydrogen, $(C_1-C_3)$alkyl and $(C_1-C_3)$alkoxy.

37. A composition of claim 28, wherein $R^3$ is selected from the group consisting of hydrogen, $(C_1-C_3)$alkyl, —$OR^{11}$ and —$NR^{11}R^{12}$, wherein $R^{11}$ and $R^{12}$ are each independently selected from the group consisting of hydrogen, $(C_1-C_3)$alkyl and $(C_1-C_3)$heteroalkyl.

* * * * *

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:cyclic
      pentapeptide
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: DISULFID
<222> LOCATION: (1)..(5)

<400> SEQUENCE: 1

Xaa Asn Gly Arg Cys
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:cyclic
      pentapeptide
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: DISULFID
<222> LOCATION: (1)..(5)

<400> SEQUENCE: 2

Xaa Asp Gly Arg Cys
  1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:cyclic
      nonapeptide
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: DISULFID
<222> LOCATION: (1)..(9)
<223> OTHER INFORMATION: disulfide bond may be from either Cys1 or
      Cys3 to either Cys7 or Cys9

<400> SEQUENCE: 3

Xaa Phe Cys Asp Gly Arg Cys Asp Cys
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:compound 28
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: MOD_RES
<222> LOCATION: (5)
<223> OTHER INFORMATION: Xaa = Cys modified by
      3-amino-4-methoxy-1-pentafluorophenylsulfonamidobenzene
<220> FEATURE:
<221> NAME/KEY: DISULFID
<222> LOCATION: (1)..(5)

<400> SEQUENCE: 4

Xaa Asn Gly Arg Xaa
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:compound 29
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: MOD_RES
<222> LOCATION: (9)
<223> OTHER INFORMATION: Xaa = Cys modified by
      3-amino-4-methoxy-1-pentafluorophenylsulfonamidobenzene
<220> FEATURE:
<221> NAME/KEY: DISULFID
<222> LOCATION: (1)..(9)

<400> SEQUENCE: 5

Xaa Phe Cys Asp Gly Arg Cys Asp Xaa
 1               5

<210> SEQ ID NO 6
<211> LENGTH: 9
<212> TYPE: PRT
<213> ORGANISM: Artificial Sequence
<220> FEATURE:
```

```
<223> OTHER INFORMATION: Description of Artificial Sequence:cyclic
      nonapeptide
<220> FEATURE:
<221> NAME/KEY: MOD_RES
<222> LOCATION: (1)
<223> OTHER INFORMATION: Xaa = N-acetyl Cys
<220> FEATURE:
<221> NAME/KEY: DISULFID
<222> LOCATION: (1)..(9)

<400> SEQUENCE: 6

Xaa Phe Cys Asp Gly Arg Cys Asp Cys
 1               5
```